United States Patent
Clement (12)

(10) Patent No.: US 6,193,672 B1
(45) Date of Patent: Feb. 27, 2001

(54) LAVAGE

(75) Inventor: Thomas P. Clement, Bloomington, IN (US)

(73) Assignee: Mectra Labs, Inc., Bloomfield, IN (US)

(*) Notice: Subject to any disclaimer, the term of this patent is extended or adjusted under 35 U.S.C. 154(b) by 0 days.

(21) Appl. No.: 09/139,634

(22) Filed: Aug. 25, 1998

Related U.S. Application Data (63) Continuation-in-part of application No. 08/573,180, filed on Dec. 15, 1995, now Pat. No. 5,797,907, which is a continuation-in-part of application No. 08/060,423, filed on May 11, 1993, now Pat. No. 5,505,210.
(60) Provisional application No. 60/072,427, filed on Jan. 26, 1998.

(51) Int. Cl.[7] .................................................. A61B 5/00
(52) U.S. Cl. ................................................... 600/565
(58) Field of Search ........................... 600/562, 564–567; 606/42, 45, 46, 49

(56) References Cited

U.S. PATENT DOCUMENTS

| | | |
|---|---|---|
| 628,907 | 7/1899 | Hart . |
| 786,215 | 3/1905 | Hepnar . |
| 811,111 | 1/1906 | Wegefarth . |
| 1,585,934 | 5/1926 | Muir . |
| 1,658,754 | 2/1928 | Wood . |
| 1,908,201 | 5/1933 | Welch et al. . |
| 2,114,695 | 4/1938 | Anderson . |
| 2,137,710 | 11/1938 | Anderson . |
| 2,148,541 | 2/1939 | Dierker . |
| 2,437,329 | 3/1948 | Moore . |
| 2,708,437 | 5/1955 | Hutchins . |
| 2,715,899 | 8/1955 | MacLean . |

(List continued on next page.)

FOREIGN PATENT DOCUMENTS

| | | |
|---|---|---|
| 3528656 | 7/1986 | (DE) . |
| 4120329 | 1/1992 | (DE) . |
| 0350291 | 5/1989 | (EP) . |
| 2332743 | 6/1977 | (FR) . |
| 991478 | 5/1965 | (GB) . |
| 8103125 | 11/1981 | (WO) . |

OTHER PUBLICATIONS

K. Semm, "Pelviscopy–Operative Guidelines", Kiel, Germany, 1988, pp. 53–54.

Pentax Precision Instrument Corp., "Gastrofiberscope", Surgical Products, Mar. 1990, vol. 9, No. 6, p. 13.

Storz, "Laparoscopic Cholescystectomy for the General Surgeon–Its Time has Come", Surgical Products, May 1990, vol. 9, No. 6, p. 13.

(List continued on next page.)

*Primary Examiner*—Max Hindenburg
(74) *Attorney, Agent, or Firm*—Barnes & Thornburg (57) ABSTRACT

A lavage for suction and removal of body tissues in a patient comprises a shield formed to include an opening, a cannula defining a cannula interior, the cannula having proximal end and a distal end. The distal end is insertable and positionable in a patient's body. The cannula defines a cannula opening to permit access to the cannula interior for the capture of body tissue in the cannula interior. The cannula is positioned to lie in the opening formed in the shield. An instrument is coupled to the cannula. A shield actuator is adapted to be engaged by a user, the shield actuator being coupled to the shield to move the shield relative to the cannula between a first position covering the instrument and a second position exposing the instrument. A valve is connected to the cannula for independent patent actuation to control irrigation and vacuum within the cannula. The cannula and valve are integrated into a rigid structure to be held in a user's hand and the valve and shield actuator are operable by the hand of the user that moves the rigidly coupled valve and cannula.

37 Claims, 8 Drawing Sheets

U.S. PATENT DOCUMENTS

| | | |
|---|---|---|
| 2,812,765 | 11/1957 | Tofflemire . |
| 2,831,174 | 4/1958 | Hilmo . |
| 2,888,928 | 6/1959 | Seiger . |
| 3,012,752 | 12/1961 | Buck . |
| 3,048,192 | 8/1962 | Murphy, Jr. . |
| 3,081,770 | 3/1963 | Hunter . |
| 3,109,426 | 11/1963 | Noonan et al. . |
| 3,157,201 | 11/1964 | Littmann . |
| 3,173,414 | 3/1965 | Guillant . |
| 3,368,734 | 2/1968 | Banko . |
| 3,404,677 | 10/1968 | Springer . |
| 3,434,691 | 3/1969 | Hamilton . |
| 3,467,082 | 9/1969 | Gilbert . |
| 3,682,177 | 8/1972 | Ames et al. . |
| 3,735,751 | 5/1973 | Katz . |
| 3,774,604 | 11/1973 | Danielsson . |
| 3,783,900 | 1/1974 | Waldbillig . |
| 3,788,602 | 1/1974 | Kitzie . |
| 3,794,032 | 2/1974 | Derouineau . |
| 3,831,607 | 8/1974 | Lindemann . |
| 3,833,000 | 9/1974 | Bridgman . |
| 3,834,372 | 9/1974 | Turney . |
| 3,837,345 | 9/1974 | Matar . |
| 3,853,127 | 12/1974 | Spademan . |
| 3,902,498 | 9/1975 | Niederer . |
| 3,910,279 | 10/1975 | Okada et al. . |
| 3,938,527 | 2/1976 | Rioux et al. . |
| 3,955,578 | 5/1976 | Chamness et al. . |
| 3,957,082 | 5/1976 | Fuson et al. . |
| 3,994,287 | 11/1976 | Turp et al. . |
| 3,995,619 | 12/1976 | Glatzer . |
| 4,011,869 | 3/1977 | Seiler, Jr. . |
| 4,011,872 | 3/1977 | Komiya . |
| 4,014,333 | 3/1977 | McIntyre . |
| 4,016,881 | 4/1977 | Rioux et al. . |
| 4,037,599 | 7/1977 | Raulerson . |
| 4,043,322 | 8/1977 | Robinson . |
| 4,073,297 | 2/1978 | Kopp . |
| 4,079,737 | 3/1978 | Miller . |
| 4,096,860 | 6/1978 | McLaughlin . |
| 4,099,529 | 7/1978 | Peyman . |
| 4,111,207 | 9/1978 | Seiler, Jr. . |
| 4,173,328 | 11/1979 | Karbo . |
| 4,177,814 | 12/1979 | Knepshield et al. . |
| 4,198,959 | 4/1980 | Otani . |
| 4,210,146 | 7/1980 | Banko . |
| 4,230,128 | 10/1980 | Aramayo . |
| 4,240,411 | 12/1980 | Hosono . |
| 4,261,357 | 4/1981 | Kontos . |
| 4,280,498 | 7/1981 | Jensen . |
| 4,282,873 | 8/1981 | Roth . |
| 4,282,884 | 8/1981 | Boebel . |
| 4,299,217 | 11/1981 | Sagae et al. . |
| 4,311,143 | 1/1982 | Komiya . |
| 4,314,560 | 2/1982 | Helfgott et al. . |
| 4,314,586 | 2/1982 | Folkman . |
| 4,379,458 | 4/1983 | Bauer et al. . |
| 4,393,872 | 7/1983 | Reznik et al. . |
| 4,397,335 | 8/1983 | Doblar et al. . |
| 4,400,168 | 8/1983 | Buechel et al. . |
| 4,414,974 | 11/1983 | Dotson et al. . |
| 4,430,081 | 2/1984 | Timmermans . |
| 4,443,220 | 4/1984 | Hauer et al. . |
| 4,444,184 | 4/1984 | Oretorp . |
| 4,445,517 | 5/1984 | Feild . |
| 4,447,235 | 5/1984 | Clarke . |
| 4,451,257 | 5/1984 | Atchley . |
| 4,468,216 | 8/1984 | Muto . |
| 4,491,132 | 1/1985 | Aikins . |
| 4,493,320 | 1/1985 | Treat . |
| 4,512,344 | 4/1985 | Barber . |
| 4,516,398 | 5/1985 | Wuchinich . |
| 4,519,385 | 5/1985 | Atkinson et al. . |
| 4,531,935 | 7/1985 | Berryessa . |
| 4,535,773 | 8/1985 | Yoon . |
| 4,540,156 | 9/1985 | Cross . |
| 4,552,146 | 11/1985 | Jensen et al. . |
| 4,553,957 | 11/1985 | Williams et al. . |
| 4,553,964 | 11/1985 | Saski . |
| 4,566,480 | 1/1986 | Parham . |
| 4,568,332 | 2/1986 | Shippert . |
| 4,577,629 | 3/1986 | Martinez . |
| 4,581,014 | 4/1986 | Millerd et al. . |
| 4,585,440 | 4/1986 | Tchervenkov et al. . |
| 4,589,414 | 5/1986 | Yoshida et al. . |
| 4,593,717 | 6/1986 | Levasseur . |
| 4,595,005 | 6/1986 | Jinotti . |
| 4,605,396 | 8/1986 | Tseo et al. . |
| 4,638,802 | 1/1987 | Okada . |
| 4,642,090 | 2/1987 | Utrata . |
| 4,642,097 | 2/1987 | Siposs . |
| 4,643,197 | 2/1987 | Greene et al. . |
| 4,644,951 | 2/1987 | Bays . |
| 4,645,496 | 2/1987 | Oscarsson . |
| 4,648,868 | 3/1987 | Hardwick et al. . |
| 4,651,753 | 3/1987 | Lifton . |
| 4,654,027 | 3/1987 | Dragan et al. . |
| 4,655,216 | 4/1987 | Tischer . |
| 4,657,018 | 4/1987 | Hakky . |
| 4,662,871 | 5/1987 | Rafelson . |
| 4,667,927 | 5/1987 | Oscarsson . |
| 4,674,500 | 6/1987 | DeSatnick . |
| 4,676,242 | 6/1987 | Doi . |
| 4,681,123 | 7/1987 | Valtchev . |
| 4,690,672 | 9/1987 | Veltrup . |
| 4,692,140 | 9/1987 | Olson . |
| 4,693,257 | 9/1987 | Markham . |
| 4,702,260 | 10/1987 | Wang . |
| 4,708,147 | 11/1987 | Haaga . |
| 4,715,360 | 12/1987 | Akui et al. . |
| 4,718,419 | 1/1988 | Okada . |
| 4,732,150 | 3/1988 | Keener, Jr. . |
| 4,735,606 | 4/1988 | Davison . |
| 4,758,235 | 7/1988 | Tu . |
| 4,793,359 | 12/1988 | Sharrow . |
| 4,798,586 | 1/1989 | Stevens . |
| 4,807,666 | 2/1989 | Morse . |
| 4,808,155 | 2/1989 | Mahurkar . |
| 4,810,244 | 3/1989 | Allen . |
| 4,874,378 | 10/1989 | Hillstead . |
| 4,881,550 | 11/1989 | Kothe . |
| 4,900,300 | 2/1990 | Lee . |
| 4,905,691 | 3/1990 | Rydell . |
| 4,911,202 | 3/1990 | Nelson . |
| 4,924,851 | 5/1990 | Ognier et al. . |
| 4,925,450 | 5/1990 | Imonti et al. . |
| 4,932,957 | 6/1990 | Zwick . |
| 4,958,621 | 9/1990 | Topel et al. . |
| 4,959,063 | 9/1990 | Kojima . |
| 4,966,551 | 10/1990 | Betush . |
| 4,985,030 | 1/1991 | Melzer et al. . |
| 4,994,067 | 2/1991 | Summers . |
| 4,994,079 | 2/1991 | Genese et al. . |
| 4,998,527 | 3/1991 | Meyer . |
| 5,002,528 | 3/1991 | Palestrant . |
| 5,011,483 | 4/1991 | Sleister . |
| 5,019,035 | 5/1991 | Missirlian et al. . |
| 5,019,054 | 5/1991 | Clement et al. . |
| 5,053,002 | 10/1991 | Barlow . |
| 5,053,044 | 10/1991 | Mueller et al. . |
| 5,071,419 | 12/1991 | Rydell et al. . |

| | | |
|---|---|---|
| 5,078,688 | 1/1992 | Lobodzinski et al. . |
| 5,078,716 | 1/1992 | Doll . |
| 5,106,364 | 4/1992 | Hayafuji et al. . |
| 5,125,910 | 6/1992 | Freitas . |
| 5,158,561 | 10/1992 | Rydell et al. . |
| 5,161,773 | 11/1992 | Tower . |
| 5,188,594 | 2/1993 | Zilberstein . |
| 5,195,958 | 3/1993 | Phillips . |
| 5,197,948 | 3/1993 | Ghodsian . |
| 5,197,963 | 3/1993 | Parins . |
| 5,217,468 | 6/1993 | Clement . |
| 5,224,929 | 7/1993 | Remiszewski . |
| 5,244,459 | 9/1993 | Hill . |
| 5,250,065 | 10/1993 | Clement . |
| 5,273,524 | 12/1993 | Fox et al. . |
| 5,275,609 | 1/1994 | Pingleton et al. . |
| 5,282,790 | 2/1994 | Clement . |
| 5,306,237 | 4/1994 | Clement et al. . |
| 5,312,332 | 5/1994 | Bales et al. . |
| 5,314,406 | 5/1994 | Arias et al. . |
| 5,335,671 | 8/1994 | Clement . |
| 5,338,292 | 8/1994 | Clement et al. . |
| 5,348,555 | 9/1994 | Zinnanti . |
| 5,350,356 | 9/1994 | Bales et al. . |
| 5,354,291 | 10/1994 | Bales et al. . |
| 5,374,244 | 12/1994 | Clement et al. . |
| 5,391,145 | 2/1995 | Dorsey, III . |
| 5,409,013 | 4/1995 | Clement . |
| 5,429,596 | 7/1995 | Arias et al. . |
| 5,437,665 | 8/1995 | Munro . |
| 5,447,494 | 9/1995 | Dorsey, III . |
| 5,449,357 | 9/1995 | Zinnanti . |
| 5,487,649 | 1/1996 | Dorsey, III et al. . |
| 5,520,634 | 5/1996 | Fox et al. . |
| 5,554,159 | 9/1996 | Fischer . |
| 5,569,244 | 10/1996 | Hahnen . |
| 5,573,504 | 11/1996 | Dorsey, III . |
| 5,607,391 | 3/1997 | Klinger et al. . |
| 5,609,573 | 3/1997 | Sandock . |

OTHER PUBLICATIONS

Pentax Precision Instrument Corp., "GI Fiberscopes", Surgical Products, May 1990, vol. 9, No. 6, p. 13.

Healthco International Handbook, 1990, p. 116.

Storz The World of Endoscopy, Semm Instruments for Operative Pelviscopy, 4th Edition, Mar. 1987, pp. 1–4.

Richard Wolf cat. pg. and sketch/admitted prior art Jan. 1992.

American Surgical Instruments, Inc., "Nexhat–Dorsey Disposable Hydro–Dissection Trumpet Valve," 3 Sheets, Mar. 19, 1990.

Richard Wolf, "The Complete Endoscopy Manufacturer", Surgical Products, May 1990, vol. 9, No. 6, p. 20.

Johnson & Johnson Medical Inc., "CIDEX is safe for scopes. Don't take our word for it." Surgical Products, May 1990, vol. 9, No. 6, p. 25.

Pentax®, "Pentax® PNEII Bronchofiberscopes", Surgical Products, May 1990, vol. 9, No. 6, p. 44.

Pentax Precision Instrument Corp., "Therapeutic Gastrofiberscope with Water Jet", Sep. 1990, vol. 10, No. 1, p. 39.

EndoDynamics, Inc., "Aspiration Device", Surgical Products, Nov. 1990, vol. 10, No. 11, p. 30.

"Irrigation/Aspiration Probe", Surgical Products, Sep. 1990, vol. 10, No. 11, p. 28.

Cabot Medical, "Laparoscopic Cholecystectomy From the Company Who Knows Laparoscopy", Surgical Products, Jan. 1991, vol. 20, No. 3, p. 4.

Olympus, "The Olympus Laparoscopic Cholecystectomy System: Resolution for Gallstones, with the leader in High–-Resolution Optics", Surgical Products, Jan. 1990, vol. 10, No. 3, p. 8.

Apple Medical, "Hunt/Reich Secondary Cannula", Surgical Products, May 1991, vol. 10, No. 7, p. 5.

Baxter Healthcare Corp., "Infusion Pump", Surgical Products, Jun. 1991, vol. 10, No. 8, p. 32.

Core Dynamics TM Inc., "Disposable Trocar with Reusable Cannula", Surgical Products, Jun. 1991, vol. 10, No. 8, p. 4.

Dexide catalog page and sketch 1991.

Halkey Roberts catalog 1990 3 pages.

Cabot Medical, "Suction/Irrigation Probe", Surgical Products, Nov. 1990, vol. 10, No. 11, p. 29.

Megadyne®—Surgical Laparoscopy & Endoscopy, vol. 3, No. 4, p. 2, 1993 Raven Press.

Nezhat–Dorsey—Journal of Laparoendoscopic Surgery, vol. 4, No. 1, Feb. 1994, Inside front cover page ISSN: 1052–3901.

Cabot—The Journal of the American Association of Gynecologic Laparoscopists, Nov., 1993, vol. 1, No. 1.

Dexide ® catalogue page "Dexide meets your Laparoscopic needs", 1991.

America Hydro–Surgical Surgery: Gynecology & Obstetrics Ad, Sep. 1993.

Ethicon Brochure, Apr. 1995.

ConMed® Aspen Surgical Systems, Surgical Products, date unknown.

FIG. 24

LAVAGE

This is a continuation in part application of U.S. patent application Ser. No. 08/573,180 to Clement, filed Dec. 15, 1995 now U.S. Pat. No. 5,797,907, which is a continuation in part application of U.S. patent application Ser. No. 08/060,423, filed May 11, 1993 and now U.S. Pat. No. 5,505,210 to Clement, issued Apr. 9, 1996. This is also a continuation in part application of U.S. Provisional Patent Application 60/072,427 filed Jan. 26, 1998.

BACKGROUND AND SUMMARY OF THE INVENTION

The present invention relates to surgical instruments. More particularly, the present invention relates to lavage assemblies for irrigation, cauterization, suction, and removal of body tissue.

Removal of tissue from a patient's body for disposal or analysis is commonly required in surgical procedures. Typically, cutting instruments have been used to separate small portions of tissue from the patient's body, and (Grasping or suction devices have been used to retrieve the tissue.

According to the present invention, a lavage is provided for suction and removal of body tissues in a patient. The lavage includes a shield, a shield actuator, a cannula, an instrument coupled to the cannula, and a valve. The shield is formed to include an opening. The cannula defines a cannula interior and has proximal and distal ends. The distal end of the cannula is insertible and positionable in a patient's body. The cannula defines a cannula opening to permit access to the cannula interior for capture of body tissue in the cannula interior. The cannula is positioned to lie in the opening formed in the shield. The shield actuator is adapted to be engaged by a user. The shield actuator is coupled to the shield to move the shield relative to the cannula between a first position wherein the shield covers the instrument and a second position wherein the shield is spaced apart from the instrument. The valve is connected to the cannula for independent actuation to control irrigation and vacuum within the cannula, regardless of movement or lack of movement of the shield. The cannula and valve are integrated into a rigid structure to be held in a user's hand such that movement of the rigidly coupled cannula and valve by the user's hand allows the distal end of the cannula to be accurately positioned at a specific location in the patient's body. The valve and shield actuator are operable by the hand of the user that moves the rigidly coupled valve and cannula to accurately position the distal end of the cannula in the patient's body.

Additional objects, features, and advantages of the invention will become apparent to those skilled in the art upon consideration of the following description of a preferred embodiment exemplifying the best mode of carrying out the invention as presently perceived.

BRIEF DESCRIPTION OF THE DRAWINGS

The detailed description particularly refers to the accompanying figures in which:

FIGS. 5–10 and 13–20 show a representative sampling of various tip instruments that can be attached to the inner cannula of the lavage of FIGS. 1–4 for monopolar electrocauterization and FIGS. 11–12 show one example of a tip instrument that can be attached to the inner cannula of the lavage of FIGS. 1b and 2b for bipolar electrocauterization, the various instruments being generally positioned to lie in the outer cannula when the outer cannula is in the extended position and positioned to lie outside of the outer cannula to perform different functions when the outer cannula is in the retracted position;

DETAILED DESCRIPTION OF THE DRAWINGS

Figures 1, 2:
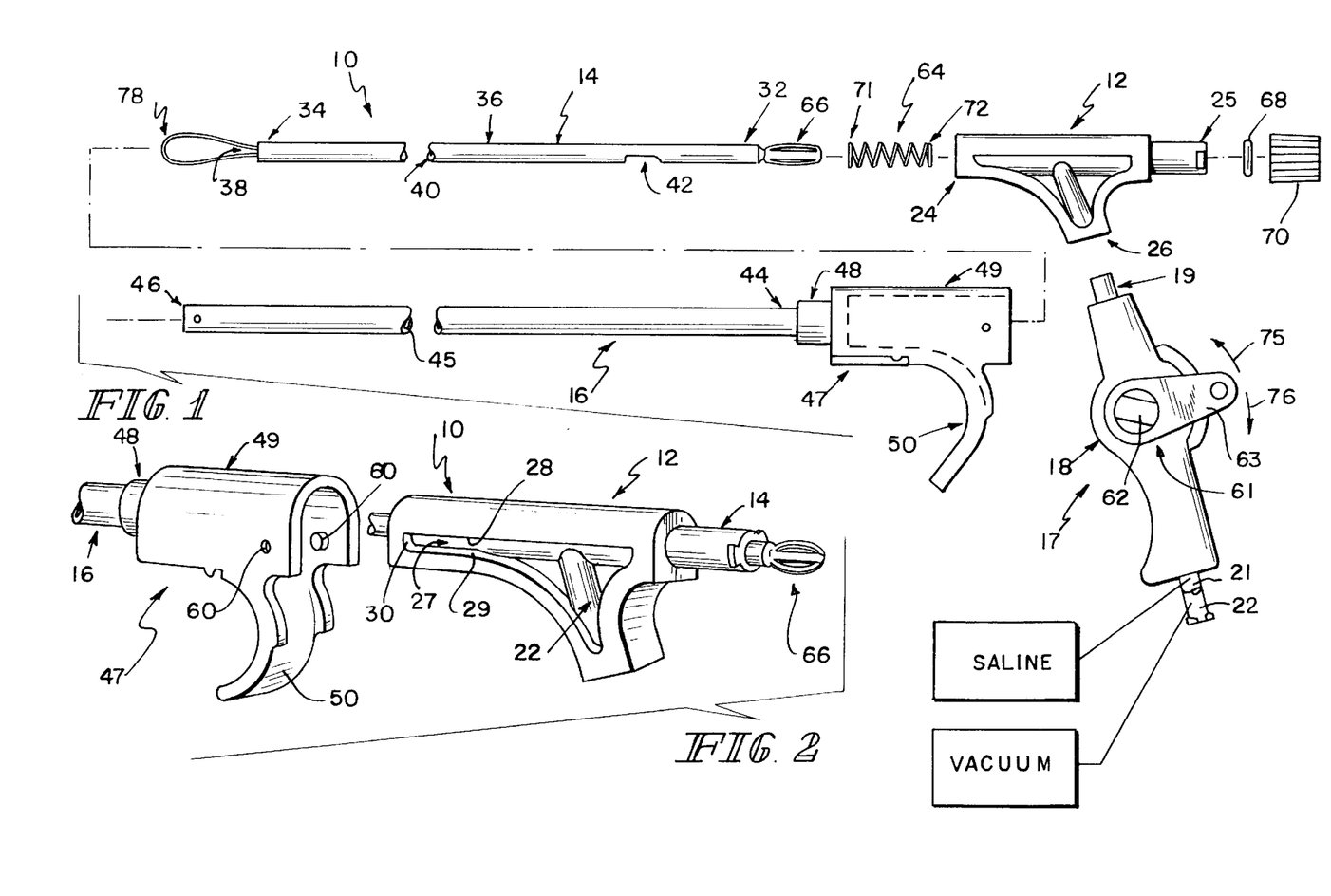
FIG. 1 is an exploded side view of an unassembled lavage for monopolar electrocauterization showing the lavage including a valve mechanism having a valve, a conduit piece being configured to receive the valve mechanism, an inner cannula having a monopolar electrical connector and being configured to extend through a spring and into the conduit piece for connection with a washer and a screw cap, and an outer cannula being configured to slide over the inner cannula and engage the conduit piece so that a trigger mounted to the outer cannula can be activated to allow the outer cannula to slide backward and forward with respect to the inner cannula.
FIG. 2 is a perspective view of a portion of the lavage of FIG. 1 partially assembled showing the inner cannula extending through the conduit piece and the outer cannula positioned to engage the inner cannula and conduit piece.

In FIG. 1, a lavage 10 for use in monopolar electrocauterization is shown in an unassembled state. Lavage 10 includes a conduit piece 12, an inner cannula 14, and an outer cannula or shield 16. The conduit piece 12 is preferably mold-formed from an elastomeric material and includes a front end 24, a back end 25, and a bottom end 26. As shown in FIG. 2, conduit piece 12 is also formed to include a pair of left and right outer slots 27 (right slot cannot be seen, but is identical to left outer slot 27 and on the opposite side of conduit piece 12 from left outer slot 27). Each slot 27 is defined by a top wall 28, a bottom wall 29, and a side wall 30.

Figure 3:
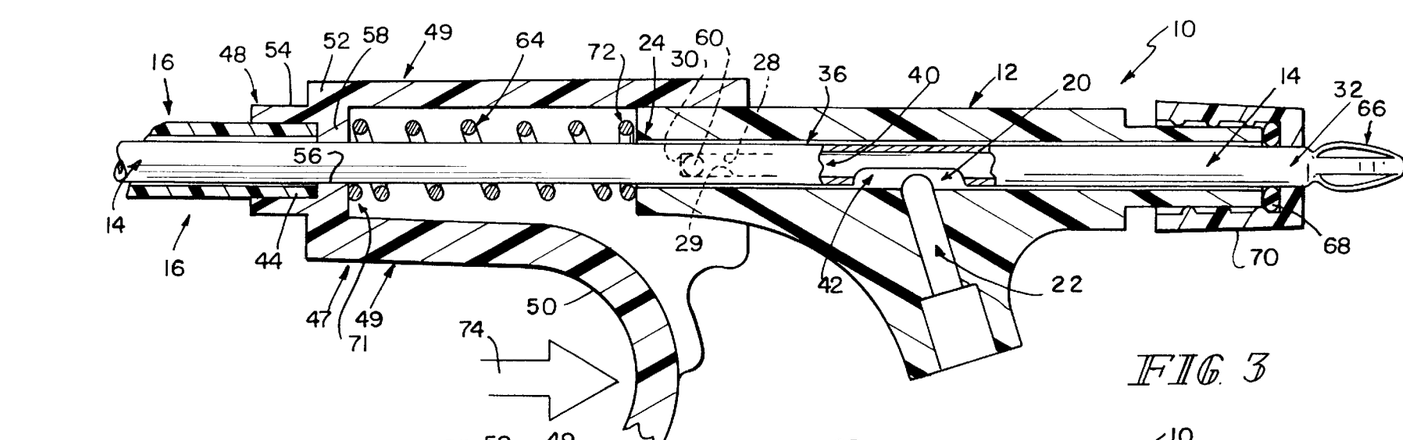
FIG. 3 is a sectional view of a portion of the lavage of FIG. 1 fully assembled showing the outer cannula in an extended position relative to the inner cannula and conduit piece with the spring biasing the outer cannula away from the conduit piece.
Figure 4:
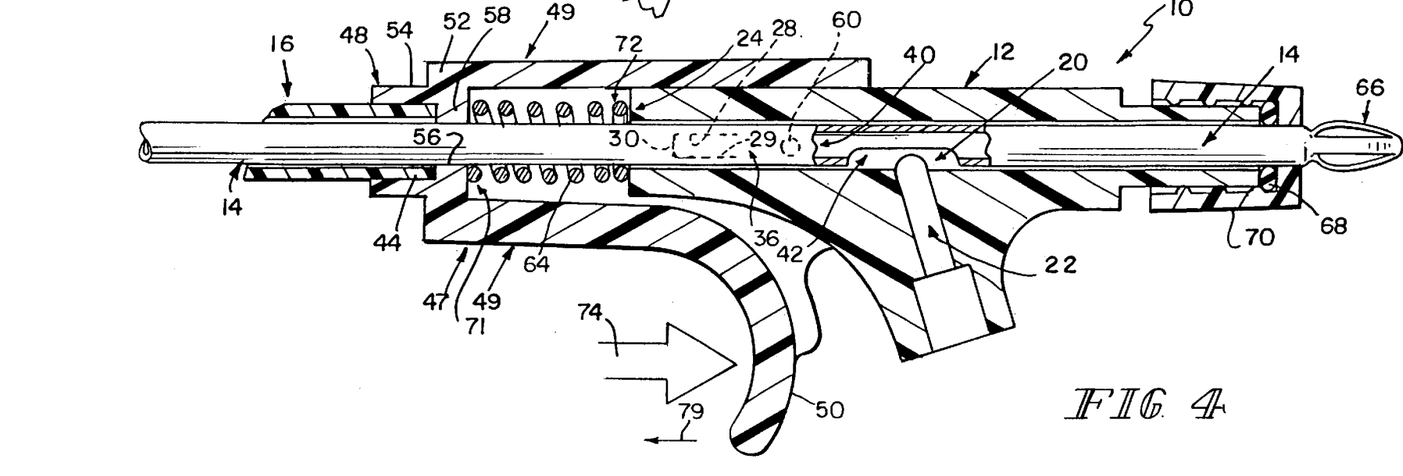
FIG. 4 is a sectional view similar to FIG. 3 showing the outer cannula in a retracted position with the trigger being pulled back toward the conduit piece to move the outer cannula toward the conduit piece.

The conduit piece 12 also includes a first channel 20 extending between front end 24 and back end 25 and a second channel 22 extending between bottom end 26 and first channel 20 as shown in FIGS. 3 and 4. The first channel 20 and second channel 22 are connected in fluid communication and the interconnection between channels 20, 22 can be characterized as a "Y-type" connection as shown in FIG. 1. However, provision of other type connections or other arrangements known in the art for fluid interconnection of channels 20, 22 is contemplated.

A valve mechanism 17 having a valve body 18 and a valve assembly 61 is coupled to lavage 10 to control the flows of fluids, gasses, and solids through the lavage 10. A preferred valve mechanism is described in U.S. Pat. No. 5,019,054 to Clement, et al., and assigned to Mectra Labs, Inc., the disclosure of which is incorporated herein by reference. Valve body 18 is coupled to conduit piece 12 such that a tube portion 19 of valve body 18 extends into second channel 22 through the bottom end 26 of conduit piece 12. Preferably, valve body 18 and conduit piece 12 are molded separately as two independent pieces as shown in FIG. 1, although, in alternative embodiments, the valve body and conduit piece could be molded together as one piece. Valve body 18 also includes a first inlet tube 21 and a second inlet tube 22 and houses valve assembly 61. First inlet tube 21 is connected to a saline source and second inlet tube 22 is connected to a vacuum source as shown in FIG. 1. Valve assembly 61 includes a rotor 62 and a thumb-engaging actuator 63.

Inner cannula 14 has a proximal end 32, a distal end 34, and a central region 36 extending therebetween. As shown in FIG. 1, inner cannula 14 extends longitudinally in a straight line, although curved, bent, flexible, or other conventional cannula designs are also contemplated. The distal end 34 of inner cannula 14 is designed for insertion into a patient's body and the proximal end 32 is connected to conduit piece 12. The central region 36 is simply the portion of inner cannula 14 between the proximal and distal ends 32, 34. Distal end 34 terminates in a tip opening 38 that allows ingress or egress of solids, liquids, or gasses from a cannula interior 40 defined by inner cannula 14. The cannula interior 40 is defined by an inner surface 41 (shown best in FIG. 5) and extends between the respective distal and proximal ends 34, 32 through the central region 36 of inner cannula 14 to accept and allow bidirectional passage therethrough of solids, liquids, or gasses.

As shown in FIGS. 3 and 4, when inner cannula 14 is affixed to conduit piece 12, the proximal end 32 of inner cannula 14 extends through a spring or biasing member 64. An electrical connector or banana plug 66 is connected to the proximal end 32 of inner cannula 14. When being assembled, electrical connector 66 extends through first channel 20 and out of the back end 25 of conduit piece 12. Furthermore, electrical connector 66 extends through an insulative washer 68 and a screw cap 70 and inner cannula 14 is connected to conduit piece 12 using washer 68 and screw cap 70. Inner cannula 14 is preferably made from a conductive metal material so that when electricity is applied to electrical connector 66, electricity will flow from the proximal end 32 to the distal end 34 of the inner cannula 14. Electrical connector 66 is soldered to inner cannula 14 so that no liquids, solids, or gases can exit the distal end 32 of inner cannula 14 during normal use. Electrical connector 66, shown in FIGS. 1–4, is used for monopolar electrocauterization where one pole of an electrocautery generator is connected to electrical connector 66 and the other pole is connected to the patient. This type of electrocauterization is used for the tip instruments shown in FIGS. 5–10 and 13–20.

Figures 1B, 2B:
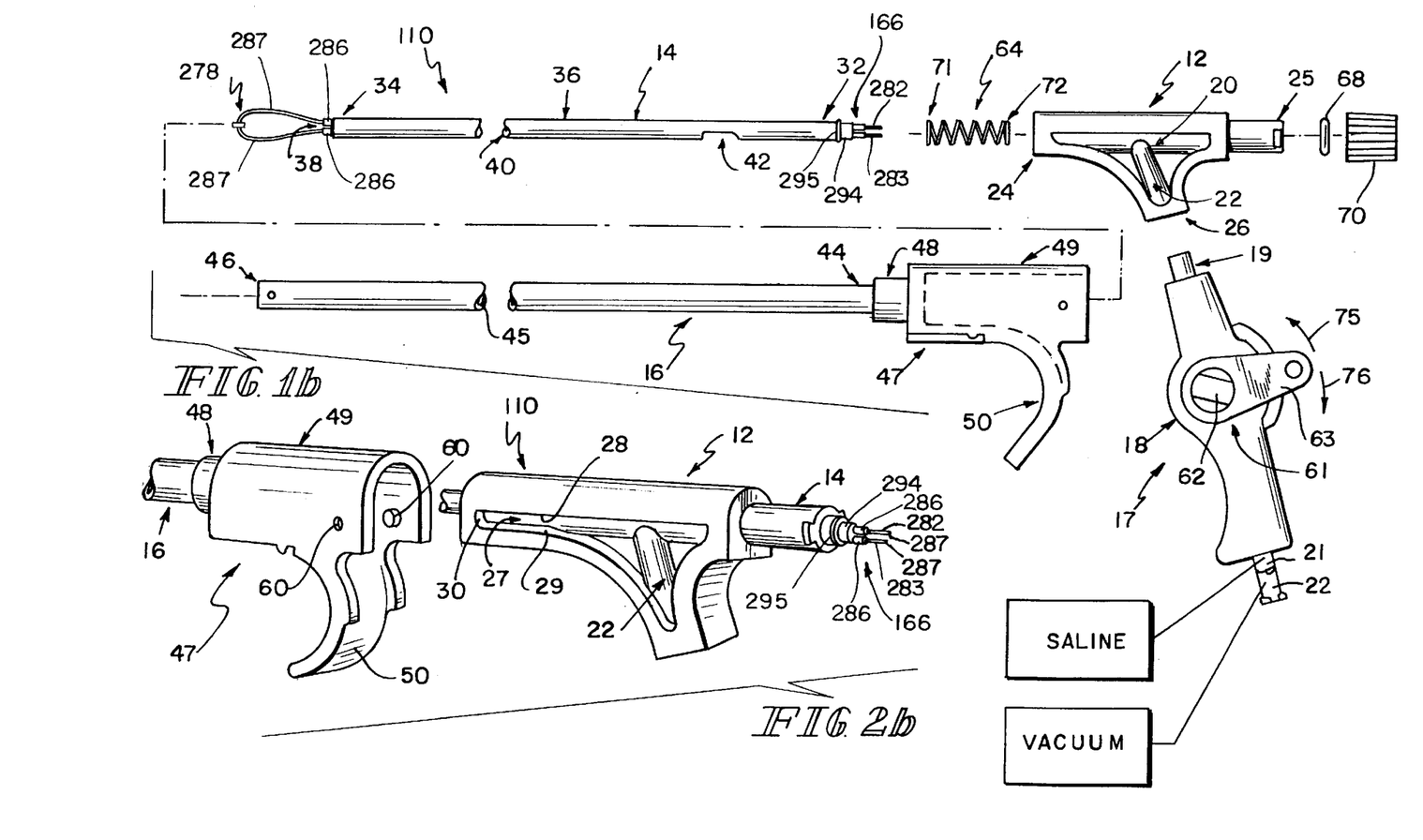
FIG. 1b is an exploded side view of an unassembled lavage for bipolar electrocauterization showing the lavage including a valve mechanism having a valve, a conduit piece being configured to receive the valve mechanism, an inner cannula having a bipolar electrical connector and being configured to extend through a spring, and into the conduit piece for connection with a washer and a screw cap, and an outer cannula being configured to slide over the inner cannula and engage the conduit piece so that a trigger mounted to the outer cannula can be activated to allow the outer cannula to slide backward and forward with respect to the inner cannula.
FIG. 2b is a perspective view of a portion of the lavage of FIG. 1b partially assembled showing the inner cannula extending through the conduit piece and the outer cannula positioned to engage the inner cannula and conduit piece.

A lavage 110 for use in bipolar electrocauterization is shown in FIGS. 1b and 2b. Bipolar lavage 110 is identical to monopolar lavage 10 (shown in FIGS. 1 and 2) except that a bipolar electrical connector 166 is used with bipolar lavage 110 while monopolar electrical connector 66 is used with monopolar lavage 10. Therefore, monopolar lavage 10 and bipolar lavage 110 have the same reference numbers, and the descriptions of each lavage applies equally to the other for everything except the electrical connectors 66 and 166.

Figure 11:
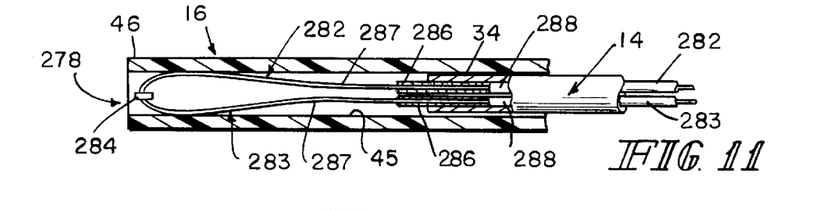
FIG. 11 is a partial sectional view showing an inner cannula for bipolar electrocauterization having a tip instrument including a pair of electrocautery electrodes interconnected with an insulator and the tip instrument being fully enclosed within the outer cannula when the outer cannula is in the extended position.
Figure 12:
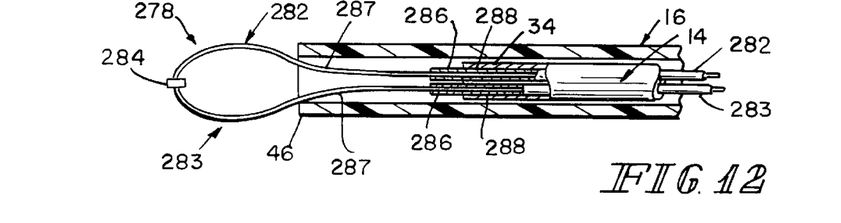
FIG. 12 is a partial sectional view showing the tip instrument of FIG. 11 being exposed when the outer cannula is in the retracted position.

As shown in FIGS. 1b and 2b, bipolar electrical connector 166 includes a first wire 282, a second wire 283, and a plug portion 294 separating first and second wires 282, 283. Bipolar electrical connector 166 is not soldered to the proximal end 32 of inner cannula 14 (as was monopolar electrical connector 66), but instead a seal 295 is used to prevent solids, liquids, or gases from escaping through the proximal end 32 of inner cannula 14 during normal use. The seal 295 may be made of potting compound, packing material, or other suitable material. As shown in FIGS. 11 and 12 (and discussed below), bipolar electrocauterization is possible when wires 282, 283 extend through the cannula interior 40 of inner cannula 14 and out the back end 25 of conduit piece 12. Seal 295 allows wires 282, 283 to exit the proximal end 32 of inner cannula 14 while maintaining an air-tight fit at the proximal end 32 of inner cannula 14. An electrocautery generator (not shown) can then be electrically connected to wires 282, 283 (since they extend through the back end 25 of conduit piece 12 as shown in FIG. 2b) to allow bipolar electrocauterization as discussed in more detail below.

Inner cannula 14 is dimensioned to conformably fit into and through the first channel 20 of conduit piece 12 and is rigidly attached to the conduit piece 12 by adhesives, welding, friction tight fit, snap fit, or other suitable attachment mechanisms. As shown in FIGS. 1, 3, and 4, an elongated aperture 42 is formed in the inner cannula 14 and positioned to allow movement of gasses, liquids, and solids between the cannula interior 40 and the second channel 22 when inner cannula 14 is affixed to conduit piece 12.

Outer cannula 16 is concentrically positioned to surround inner cannula 14. The inner diameter of outer cannula 16 is substantially equal to the outer diameter of inner cannula 14 to provide a close, sliding engagement between the inner and outer cannulas 14, 16. Outer cannula 16 includes a proximal end 44 and a distal end 46. The proximal end 44 of outer cannula 16 is coupled to a trigger portion or shield actuator 47. Trigger portion 47 includes a cup portion 48 for engaging outer cannula 16, a trigger 50 for engaging a digit of a hand operating the lavage 10, and an outer shell 49 interconnecting the cup portion 48 and trigger 50.

In preferred embodiments, trigger portion 47 is mold-formed from an elastomeric material such that cup portion 48, outer shell 49, and trigger portion 50 are all one piece, although they could be made as separate pieces. Outer cannula 16 is also preferably made from elastomeric material and is glued to trigger portion 47, although any suitable fastening means such as welding, press-type fit, or snap-fit could be used. Conduit piece 12 and valve body 18 are also preferably formed from an elastomeric material.

As shown best in FIG. 3, cup portion 48 includes a circular base member 52 and a cylindrical side wall 54. The inner diameter of the cylindrical side wall 54 is substantially equal to the outer diameter of outer cannula 16. The circular base member 52 includes a central aperture 56 having a diameter substantially equal to the outer diameter of the inner cannula 14. Circular base member 52 and cylindrical side wall 54 cooperate to form a shoulder 58. Outer cannula 16 is inserted into cup portion 48 until proximal end 44 of outer cannula 16 abuts shoulder 58 to connect outer cannula 16 and trigger portion 47. Outer cannula 16 and trigger portion 47 slidably engage inner cannula 14 as a unit, as shown in FIGS. 3 and 4. Preferably, outer shell 49 is formed to include a pair of inwardly-extending projections 60 (shown in FIG. 2 and in phantom in FIGS. 3 and 4) so that projections 60 can engage the top, bottom, and side walls 28, 29, 30 that define slot 27 formed in conduit piece 12 to hold outer cannula 16 to conduit piece 12. The trigger 50 is adapted to be engaged by a digit of a surgeon's hand.

Figure 5:
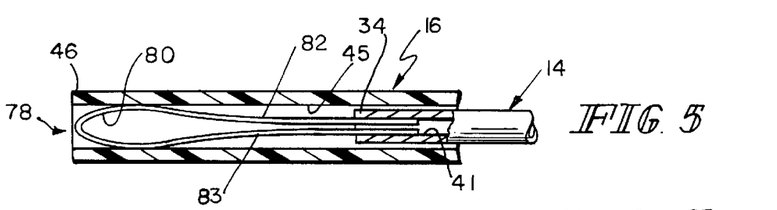
FIG. 5 is a partial sectional view showing an inner cannula for monopolar electrocauterization having a tip instrument including a loop portion and two legs, the tip instrument being completely enclosed within the outer cannula when the outer cannula is in the extended position before the trigger is pulled back toward the conduit piece.
Figure 6:
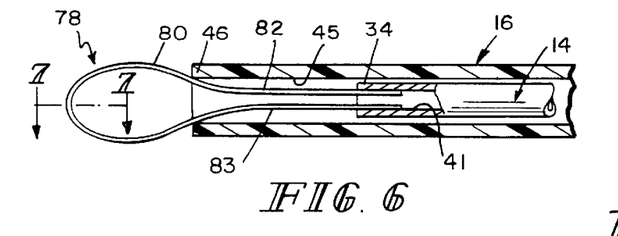
FIG. 6 is a partial sectional view showing the inner cannula and tip instrument of FIG. 5 with the outer cannula in the retracted position thereby exposing the loop portion of the tip instrument.

Before trigger 50 is engaged and pulled back by a surgeon, outer cannula 16 and trigger portion 47 are in an extended position away from conduit piece 12 because spring 64 biases outer cannula 16 and trigger portion 47 away from conduit piece 12 as shown in FIG. 3. In the extended position, a first end 71 of spring 64 pushes against shoulder 58 of trigger portion 47 and a second end 72 of spring 64 pushes against the front end 24 of conduit piece 12. Because trigger 50 has not yet been pulled back, conduit piece 12 and outer cannula 16 are in a maximum spaced-apart relation to one another with projections 60 of trigger portion 47 abutting side wall 30 of conduit piece 12. In this position, as described below and shown in FIG. 5, tip instrument 78 is completely contained within outer cannula 16. However, when a surgeon pulls back on trigger 50, outer cannula 16 and trigger portion 47 move to a retracted position as shown in FIG. 4. In the retracted position, spring 64 is compressed between shoulder 58 of trigger portion 47 and front end 24 of conduit piece 12 so that projections 60 no longer abut side walls 30 of conduit piece 12 (shown in phantom in FIG. 4). In the retracted position, tip instrument 78 of FIG. 1 is exposed beyond the distal end 46 of outer cannula 16, as shown in FIG. 6, so that the surgeon can use tip instrument 78 as desired.

In operation, distal ends 34, 46 of inner and outer cannulas 14, 16, respectively, of lavage 10 are inserted into a patient's body by conventional means. Initially, as the surgeon is inserting lavage 10, outer cannula 16 is in the extended position (before the surgeon pulls back on trigger 50) with first end 71 of spring 64 pushing shoulder 58 of trigger portion 47 away from conduit piece 12 and projections 60 abutting side walls 30, as shown in FIG. 3. FIG. 5 shows the corresponding position of tip instrument 78 relative to outer cannula 16 when outer cannula 16 is in the extended position. Thus, tip instrument 78 is not exposed as the surgeon positions lavage 10 at an operation site in a patient's body.

When lavage 10 is properly positioned at the operating site, the surgeon moves thumb-engaging actuator 63 in a first direction 75 to permit saline solution or other irrigation fluid to flow to the site. The surgeon may also move thumb-engaging actuator 63 in a second direction 76 to draw a vacuum on the operation site in addition to or in place of using the saline solution. When the site is sufficiently clear, the surgeon can turn off the irrigation fluid or vacuum (by moving thumb-engaging actuator 63 to the middle position shown in FIG. 1) and pull trigger 50 toward conduit piece 12. Because the surgeon's hand is holding valve mechanism 17 which is connected to conduit piece 12, conduit piece 12 and inner cannula 14 can be held in a fixed position. Then, when the surgeon uses his finger to pull back on trigger 50, outer cannula 16 moves towards the retracted position with spring 64 slightly resisting the movement of the surgeon's digit. Pulling trigger 50 toward the retracted position moves trigger portion 47 and outer cannula 16 away from the normal, or at rest, configuration (i.e., the extended position) in direction 74 as shown in FIG. 3. As outer cannula 16 slides along inner cannula 14, tip instrument 78 begins to be exposed. As the trigger 50 is pulled further in the direction of arrow 74, the outer cannula 16 reaches a fully-retracted position with the tip instrument 78 being fully exposed as shown in FIG. 6. With the tip instrument 78 exposed within the patient's body, tip instrument 78 can be used as a cutting or scraping, device or as a snare. With one hand, a surgeon can properly position lavage 10, operate actuator 63 to provide irrigation and vacuum functions, and actuate trigger 50 to retract outer cannula 16 and expose instrument 78.

After the surgeon is finished performing the desired operation, the surgeon (while continuing to pull back on trigger 50) can move thumb-engaging actuator 63 in the second direction 76 to connect the vacuum source to the inner cannula 14 through first channel 20 and aperture 42. The vacuum draws the cut tissue through the cannula interior 40, the elongated aperture 42, and first channel 20. Once removed, the cut tissue can be stored for later analysis or disposal. Thereafter, if the wound is a bleeder, electricity could be used to cauterize the wound. Electricity is provided to the electrical connector 66 (usually through a foot pedal switch coupled to an electrocautery (generator—not shown) so that electricity can flow through inner cannula 14 to tip instrument 78. Thus, tip instrument 78 can be used for cauterization as well as cutting and scraping. Once the operation process is complete, the surgeon releases trigger 50 so that the first end 71 of spring 64 pushes shoulder 58 of outer cannula 16 in direction 79 as shown in FIG. 4 away from conduit piece 12. This causes outer cannula 16 to enclose tip instrument 78 thereby preventing accidental cutting or scraping as the lavage 10 is removed from the patient. Outer and inner cannulas 14, 16 could then be removed from the patient's body and disposed of properly or rearranged for other functions as described below.

Although tip instrument 78 is shown as a loop in FIGS. 1, 5, and 6, a number of different tip configurations can be used with the inner cannula of the present invention. As shown in FIGS. 5–20, there are seven tip instruments or configurations that are particularly useful. These tip instruments, along with many other tip instruments or configurations, can be connected to the removable inner cannula to provide a family of removable inner cannulas for performing various functions. These various inner cannulas can then be quickly connected and disconnected by a surgeon during operation.

As shown in FIGS. 5–20, each tip instrument is enclosed within an outer cannula when the outer cannula and trigger portion are in the extended state (i.e., when the trigger has not been pulled back). However, when the trigger is pulled back by a surgeon, the trigger portion and the outer cannula are in the retracted position and the tip instruments are exposed. Each of the preferable tip instruments for use with either a monopolar or bipolar electrocautery lavage are described below. In alternative embodiments, other tip instruments can be attached to an inner cannula.

Inner and outer cannulas 14, 16 shown in FIGS. 5–20 are identical to the inner and outer cannulas 14, 16 shown in FIGS. 1–4, 1b, and 2b. In FIGS. 5–10 and 13–20, a monopolar electrical connector 66 (as shown in FIGS. 1 and 2) is used and the various tip instruments are fastened to the distal end 34 of inner cannula 14 to make the monopolar electrical connection. Conversely, in FIGS. 11 and 12, a bipolar electrical connector 166 (shown in FIGS. 1b and 2b) is used and the tip instrument has two wires 282, 283 that extend through the cannula interior 40 to make the bipolar electrical connection. Although FIGS. 5–10 and 13–20 show monopolar electrocautery tip instruments, each of these tip instruments can be configured in a manner similar to that shown in FIGS. 1b, 2b, and 11–12 for use in a bipolar electrocauterization system.

A first embodiment of tip instrument 78 connected to the distal end 34 of inner cannula 14 is shown in FIGS. 1 and 5–8. Tip instrument 78 includes a pair of legs 82, 83 and a loop portion 80 extending between legs 82, 83. Legs 82, 83 are connected to the inner surface 41 of inner cannula 14 at the distal end 34 of inner cannula 14 so that tip instrument 78 extends outwardly away from the distal end 34 of inner cannula 14 toward distal end 46 of outer cannula 16 as shown in FIGS. 5 and 6. Loop portion 80 is substantially oval-shaped. When outer cannula 16 is in the extended state (as shown in FIG. 5), loop portion 80 is flattened by cannula interior 40 so that the entire tip instrument 78 is contained within outer cannula 16. When outer cannula 16 is in the retracted position thereby exposing tip instrument 78 (as shown in FIG. 6), loop portion 80 expands radially outwardly so that the surgeon is able to lasso varying sizes of tissue depending on how far the surgeon pulls back on trigger 50.

As can be appreciated from FIGS. 5 and 6, the surgeon can operate trigger 50 to expose any amount of tip instrument 78. As shown in FIG. 5, none of loop portion 80 is exposed because trigger 50 has not been pulled back and the entire tip instrument 78 is enclosed in outer cannula 16. However, as the surgeon begins to pull back on trigger 50, outer cannula 16 retracts thereby causing tip instrument 78 to become partially exposed. Of course, as tip instrument 78 becomes exposed, loop portion 80 will expand radially outwardly until it reaches its fully-opened position shown in FIG. 6. Then, by releasing trigger 50, the surgeon can make the loop portion 80 smaller, thereby using loop portion 80 as a lasso.

Figures 7, 8:
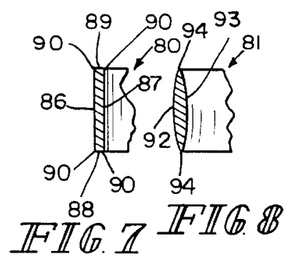
FIG. 7 is a sectional view taken along line 7—7 of FIG. 6 showing the loop of FIGS. 5 and 6 including rectangular-shaped edges.
FIG. 8 is a sectional view similar to FIG. 7 showing a second embodiment of the loop of FIGS. 5 and 6 including double convex-shaped edges.

The cross section of loop portion 80 may be either rectangular as shown in FIG. 7 or elliptical or double convex as shown in FIG. 8. The rectangular and double convex cross sections substantially prevent the build up of material from the cauterizing or burning process. As shown in FIG. 7, loop portion 80 having a rectangular cross section includes a smooth outer surface 86, a smooth inner surface 87, and two smooth side surfaces 88, 89 interconnecting outer surface 86 and inner surface 87. Loop portion 80 also includes four corners or edges 90 where smooth side surfaces 88, 89 meet smooth outer and inner surfaces 86, 87. A rectangular wire is particularly advantageous for loops because this cross section does not twist when bent, cuts well when used as a snare, cuts and scrapes well using the edges 90 on the outside of the loop, and presents desirable flat surfaces 86, 87, 88, 89 for cauterization when the loop portion 80 is slightly exposed beyond the distal end 46 of the outer cannula 16. As shown in FIG. 8, loop portion 81 having a double convex cross section includes a smooth outer surface 92, a smooth inner surface 93, and two corners or edges 94 interconnecting smooth outer and inner surfaces 92, 93. Although rectangular and double convex cross sections are preferable, a variety of other cross sectional shapes can be used that provide smooth surfaces.

Figure 9:
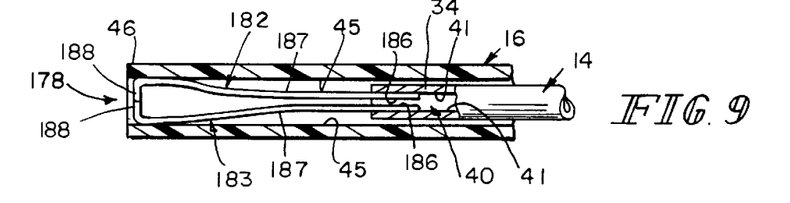
FIG. 9 is a partial sectional view showing an inner cannula for monopolar electrocauterization having a tip instrument being a grasper and the outer cannula being in the extended position such that the grasper is fully enclosed within the outer cannula.
Figure 10:
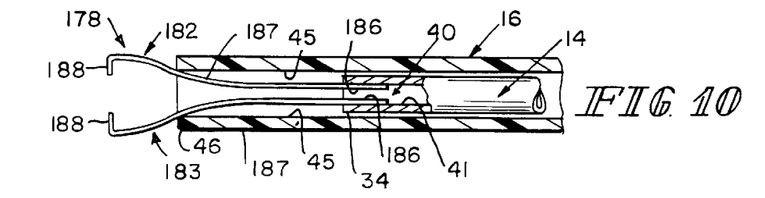
FIG. 10 is a partial sectional view showing the grasper of FIG. 9 with the outer cannula being in the retracted position to expose the grasper.

A second embodiment of a tip instrument 178 is shown in FIGS. 9 and 10. Tip instrument 178 (also referred to as a grasper or wire pincer 178) includes a first leg 182 and a second leg 183. First and second legs 182, 183) each include a hip portion 186, a leg portion 187, and a foot portion 188. Each hip portion 186 is tack-welded to the inner surface 41 of cannula interior 40 at the distal end 34 of inner cannula 14. Each leg portion 187 extends outwardly from hip portion 186 away from distal end 34 of inner cannula 14 and terminates at the foot portion 188. Each foot portion 188 is substantially perpendicular to its respective leg portion 187 and faces inwardly so that foot portion 188 of first leg 182 and foot portion 188 of second leg 183 face one another as shown in FIG. 10.

Each leg portion 187 is configured to bow outwardly so that when outer cannula 16 is in the retracted position, legs 182, 183 are spaced apart from one another thereby opening wire pincer 178, as shown in FIG. 10. Conversely, with outer cannula 16 in the retracted position, legs 182, 183 are pinched together by inner surface 45 of outer cannula 16 so that foot portions 188 of legs 182, 183 abut as shown in FIG. 9. As a result, as trigger 50 is used to move outer cannula 16 from the retracted position to the extended position or vice versa, wire pincer 178 can be opened and closed to grab or pinch tissue during operation. Although not shown, wire pincer 178 can also have a rectangular or double convex cross section, as shown for wire loop 78 in FIGS. 7 and 8, or any other type of cross section. In addition, although wire pincer 178 is preferably made from a conductive metal material (for cauterization purposes), other types of material such as plastic could be used.

A third embodiment of a tip instrument 278 is shown in FIGS. 11 and 12. Tip instrument 278 (also referred to as bipolar electrocautery electrodes 278) includes a first wire 282, a second wire 283, and an insulator 284 interconnecting first and second wires 282, 283. Unlike tip instruments 78 and 178, tip instrument 278 is not welded to the inner surface 41 of inner cannula 14. Instead, first and second wires 282, 283 extend through the cannula interior 40 of inner cannula 14 and out the back end 25 of conduit piece 12 to connect to a bipolar electrocautery generator (not shown). As mentioned above, seal 295 is used to seal the proximal end 32 of inner cannula 14 against leaks. First and second wires 282, 283 each include an insulated portion 286 and an exposed portion 287. Each insulated portion 286 includes an insulated wire cover 288 that insulates the respective first and second wires 282, 283. Insulated portion 286 preferably extends beyond the distal end 34 of inner cannula 14 as shown in FIGS. 11 and 12. Each exposed portion 287 extends from the end of each insulated portion 286 away from inner cannula 14 and terminates at insulator 284. Exposed portions 287 are bare wires and are configured to bow outwardly so that a loop is formed when outer cannula 16 is retracted as shown in FIG. 12. This allows tip instrument 278 to be used as a lasso to grab various pieces of tissue by operating trigger 50 to open and close the loop. In addition, by separating first wire 282 from second wire 283 using insulator 284, bipolar cauterization can be accomplished when electricity is supplied to the wires 282, 283. Although not shown, tip instrument 278 can also have a rectangular or double convex cross section, as shown for wire loop 78 in FIGS. 7 and 8, or any other type of cross section.

Figure 13:
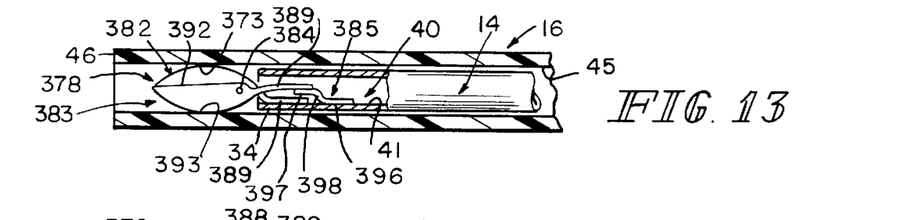
FIG. 13 is a partial sectional view showing an inner cannula for monopolar electrocauterization having a tip instrument being scissors and the scissors being fully enclosed within the outer cannula when the outer cannula is in the extended position.
Figures 14, 15:
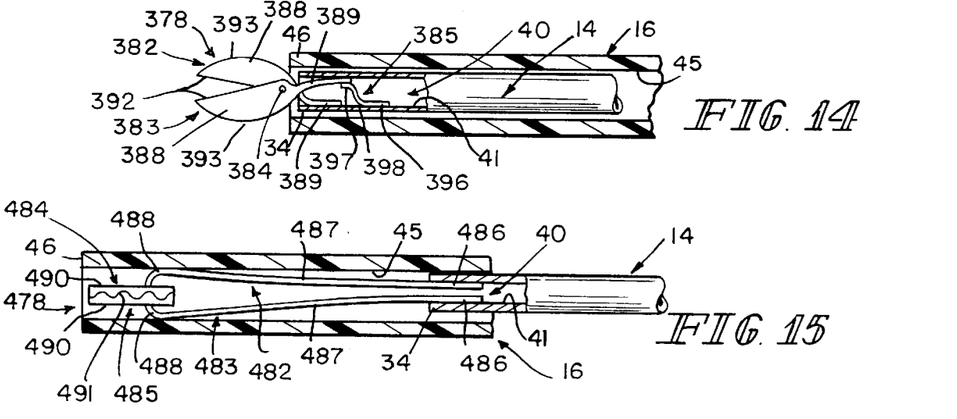
FIG. 14 is a partial sectional view showing the scissors of FIG. 13 being exposed when the outer cannula is in the retracted position.
FIG. 15 is a partial sectional view showing an inner cannula for monopolar electrocauterization having a tip instrument being forceps and the forceps being fully enclosed within the outer cannula when the outer cannula is in the extended position.

A fourth embodiment of a tip instrument 378 is shown in FIGS. 13 and 14. Tip instrument 378 (also referred to as scissors 378) includes a first blade 382, a second blade 383, a rivet 384 interconnecting first and second blades 382 383, and a spring mechanism 385. First and second blades 382, 383 are pivotably connected together by rivet 384 so that when outer cannula 16 is in the extended position as shown in FIG. 13, blades 382, 383 are pinched together. When outer cannula 16 is in the retracted position, however, as shown in FIG. 14, blades 382, 383 are opened.

First and second blades 382, 383 each include a cutting portion 388 and a handle portion 389. Each cutting portion 388 includes a cutting surface 392 and a cannula-engaging, surface 393. Each cannula-engaging surface 393 is designed to engage the inner surface 45 of outer cannula 16 when trigger 50 is operated so that the scissors 378 can open and close as shown in FIGS. 13 and 14 allowing cutting portions 388 to cut desired tissue. The handle portions 389 are connected to their respective cutting portions 388 and reside within the cannula interior 40 of inner cannula 14. The handle portion 389 of first blade 382 is welded to the inner surface 41 of inner cannula 14 as shown in FIGS. 13 and 14. The handle portion 389 of second blade 383 is not welded to the inner surface 41 of inner cannula 14, but instead is free to move within cannula interior 40 limited only by spring mechanism 385.

Spring mechanism 385 is welded to the inner surface 41 of inner cannula 14 and biases handle portion 389 of second blade 383 upwardly away from handle portion 389 of first blade 382 so that scissors 378 are in the open position when outer cannula 16 is in the retracted position as shown in FIG. 14. Spring mechanism 385 is S-shaped and includes a first leg 396 welded to interior surface 41, a second leg 397, and a middle portion 398 interconnecting first and second legs 396, 397. Second leg 397 pushes upwardly against handle portion 389 of second blade 383 as shown in FIG. 14.

A user cuts tissue with scissors 378 by retracting and releasing trigger 50. As trigger 50 is released from the retracted position so that outer cannula 16 begins to enclose scissors 378, cannula-engaging surfaces 393 of first and second blades 382, 383 bump against the inner surface 45 of outer cannula 16. This forces first and second blades 382, 383 to be pushed together, thereby allowing cutting surfaces 392 to cut tissue. This also causes handle portion 389 of second blade 383 to press downwardly on the second leg 397 of spring mechanism 385 as shown in FIG. 13. Thus, scissors 378 can be opened and closed by using trigger 50 to move outer cannula 16 back and forth.

Figure 16:
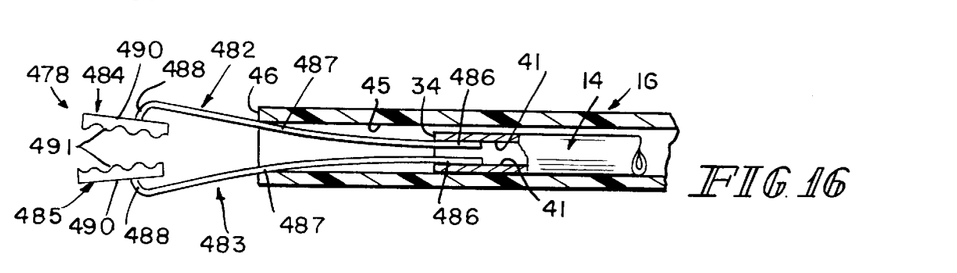
FIG. 16 is a partial sectional view showing the forceps of FIG. 15 being exposed when the outer cannula is in the retracted position.

A fifth embodiment of a tip instrument 478 is shown in FIGS. 15 and 16. Tip instrument 478 (also referred to as graspers 478) includes a first leg 482, a second leg 483, a first foot 484 connected to first leg 482, and a second foot 485 connected to second leg 483. First and second legs 482, 483 each include a hip portion 486, a leg portion 487, and an ankle portion 488. Each hip portion 486 is connected to the inner surface 41 of cannula interior 40 at the distal end 34 of inner cannula 14. Preferably, each hip portion 486 is tack-welded, although any connection mechanism or method can be used. Each leg portion 487 extends outwardly from hip portion 486 away from distal end 34 of inner cannula 14 and terminates at the ankle portion 488. Connected to each ankle portion 488 is the respective foot 484, 485. Preferably, ankle portions 488 are bent inwardly toward each other so that feet 484, 485 can mate with one another as shown in FIGS. 15 and 16. Each foot 484, 485 includes a flat portion 490 for connecting to ankle portion 488 of legs 482, 483 and a toothed portion 491 for grasping items. As shown in FIGS. 15 and 16, grasper 478 can be opened and closed by activating trigger 50 to move outer cannula 16 forward and backward relative to inner cannula 14 so that feet 484, 485 can open and close to grasp tissue in between each toothed portion 491.

Figures 17, 18:
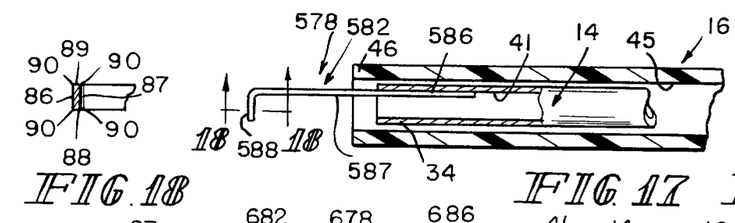
FIG. 17 is a partial sectional view showing an inner cannula for monopolar electrocauterization having a tip instrument being an "L-hook" and the L-hook being exposed when the outer cannula is in the retracted position.
FIG. 18 is a sectional view taken along line 18—18 of FIG. 17 showing the hook of FIG. 17 including rectangular-shaped edges.
Figure 19:
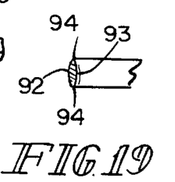
FIG. 19 is a sectional view similar to FIG. 18 showing a second embodiment of the L-hook of FIG. 17 including double convex-shaped edges.

A sixth embodiment of a tip instrument 578 is shown in FIGS. 17–19. Tip instrument 578 (also referred to as L-hook 578) includes a single leg 582 having a hip portion 586 welded to inner surface 41, a leg portion 587 extending outwardly away from the distal end 34 of inner cannula 14 from hip portion 586, and a foot portion 588 extending perpendicularly away from the leg portion 587. Like the other tip instruments, the L-hook 578 is exposed when outer cannula 16 is retracted and is enclosed within outer cannula 16 when outer cannula 16 is extended. As shown in FIGS. 18 and 19, L-hook 578 is preferably formed to have a rectangular or double convex cross section, respectively. The components of the rectangular and double convex cross section wire shown in FIGS. 18 and 19, respectively, are identical to and thus numbered identical as the components of the rectangular and double convex cross section wire shown in FIGS. 7 and 8. Although a rectangular or double convex cross section is preferable, any other type of cross section may be used.

Figures 20, 21, 22:
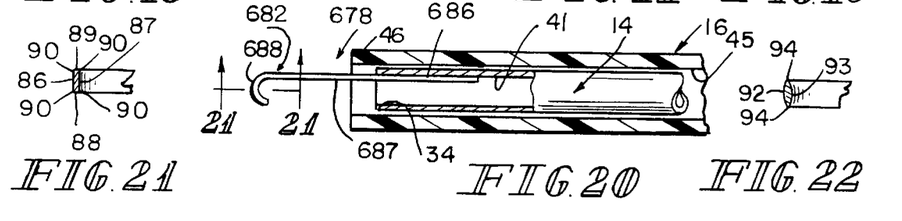
FIG. 20 is a partial sectional view showing an inner cannula for monopolar electrocauterization having a tip instrument being a "J-hook" and the J-hook being exposed when the outer cannula is in the retracted position.
FIG. 21 is a sectional view taken along line 21—21 of FIG. 20 showing the J-hook of FIG. 20 including square-shaped edges.
FIG. 22 is a sectional view similar to FIG. 21 showing a second embodiment of the J-hook of FIG. 20 including double convex-shaped edges.

A seventh embodiment of a tip instrument 678 is shown in FIGS. 20–22. Tip instrument 678 (also referred to as J-hook 678) includes a single leg 682 having a hip portion 686 welded to inner surface 41, a leg portion 687 extending outwardly away from the distal end of inner cannula 14 from hip portion 686, and a foot portion 688 extending from the leg portion 687 to form a "J" shape. Like the other tip instruments, J-hook 678 is exposed when outer cannula 16 is retracted and is enclosed within outer cannula 16 when outer cannula 16 is extended. As shown in FIGS. 21 and 22, J-hook 678 is preferably formed to have a rectangular or double-convex cross section, respectively. The components of the rectangular and double-convex cross section wire shown in FIGS. 21 and 22, respectively, are identical to and thus numbered identical as the components of the rectangular and double-convex cross section wire shown in FIGS. 7 and 8. Although a rectangular or double convex cross section is preferable, any other type of cross section may be used.

Another preferred embodiment of a lavage 410 is shown in FIGS. 23–26. Lavage 410 includes a conduit piece 412, an inner cannula 414, an outer cannula or shield 416, a valve mechanism 418, a trigger portion or shield actuator 420 coupled to outer cannula 416 and an instrument 422 coupled to inner cannula 414. The valve mechanism 418 is identical to valve mechanism 17 of lavage 10 and thus the reference numbers and description of valve mechanism 17 applies to valve mechanism 418. The instrument 422 may be any of the instruments shown in FIGS. 5–22.

Figure 23:
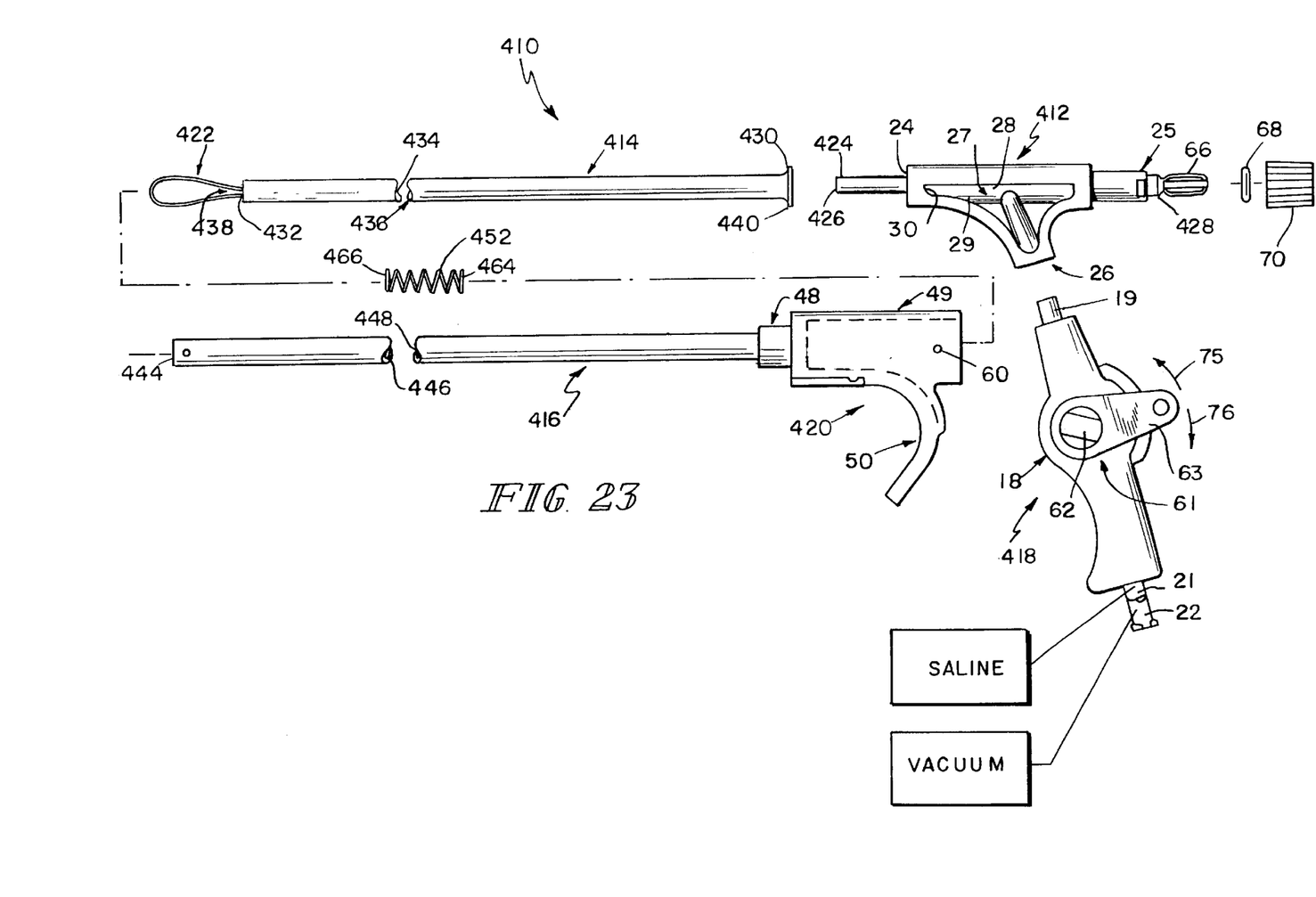
FIG. 23 is an exploded view of yet another embodiment of a lavage according to the present invention, the lavage including a valve mechanism having a valve, a conduit piece being configured to receive the valve mechanism, an inner cannula configured to extend through a spring and into the conduit piece, an instrument coupled to the inner cannula, and an outer cannula being configured to slide over the inner cannula and engage the conduit piece so that a trigger mounted on the outer cannula can be activated to allow the outer cannula to slide backward and forward relative to the inner cannula.

The conduit piece 412 is identical to conduit piece 12 of lavage 10 except that conduit piece 412 includes a support tube 424 extending through first channel 20 of conduit piece 412. Except for support tube 424, the reference numbers and description of conduit piece 12 applies to conduit piece 412.

The support tube 424 includes a first end 426 positioned to lie within trigger portion 420 and a second end 428 spaced apart from first end 426. The support tube 424 is tapered so that the first end 426 is larger than the second end 428.

The trigger portion 420 is identical to trigger portion 47 of lavage 10 except that trigger portion 420 does not include a shoulder 58. Except for shoulder 58, trigger portion 420 is identical to trigger portion 47.

Inner cannula 414 includes a proximal end 430 positioned adjacent to conduit piece 412 and trigger portion 420 and a distal end 432 spaced apart from conduit piece 412 and trigger portion 420. Inner cannula 414 further includes an inner surface 434 that defines an interior region 436 and a tip opening 438 at distal end 432. The proximal end 430 of inner cannula 414 includes a flange 440.

Figure 24:
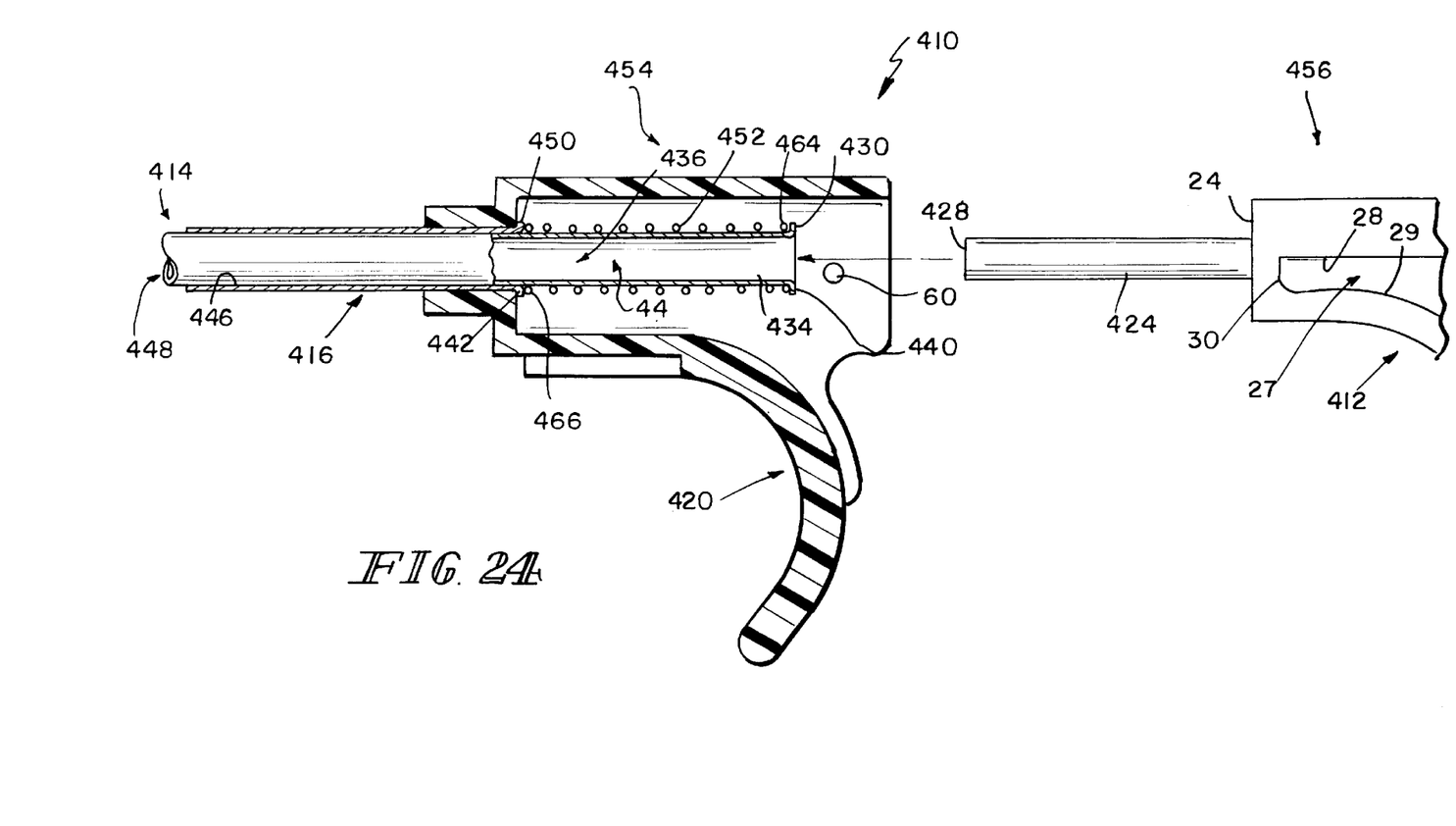
FIG. 24 is a partial sectional view showing the outer cannula, inner cannula, and trigger comprising a first instrument portion of the lavage and the conduit piece comprising a second handle portion of the lavage, the conduit piece is formed to include a slot, and the outer cannula is formed to include a detent that is configured to snap fit into the slot so that a variety of different first instrument portions can be connected to the second handle portion of the lavage.
Figure 25:
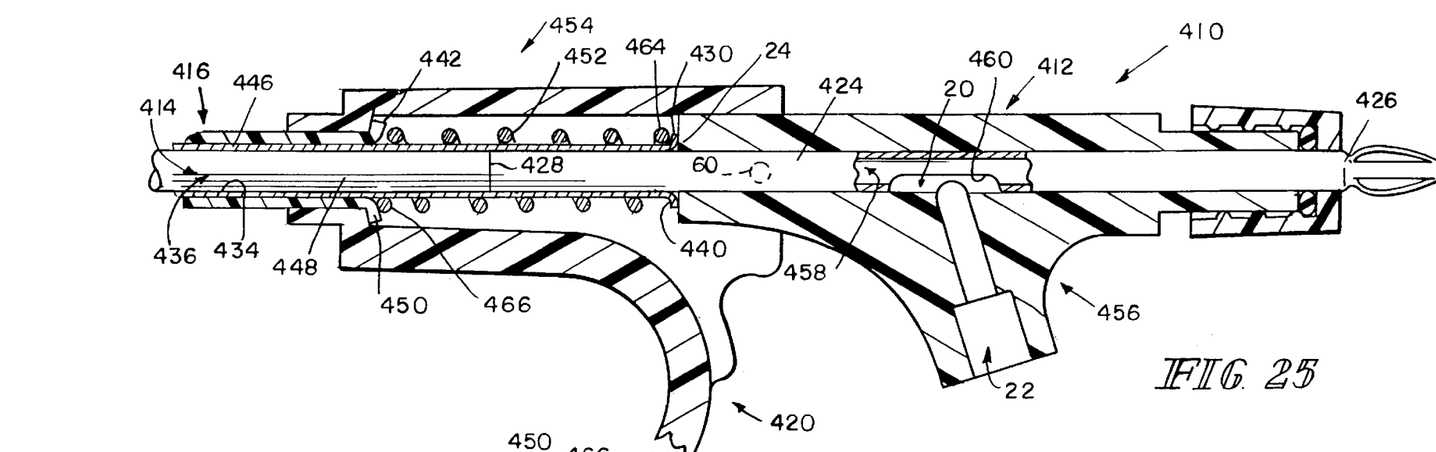
FIG. 25 is a partial sectional view showing the first portion of the lavage connected to the second portion of the lavage.
Figure 26:
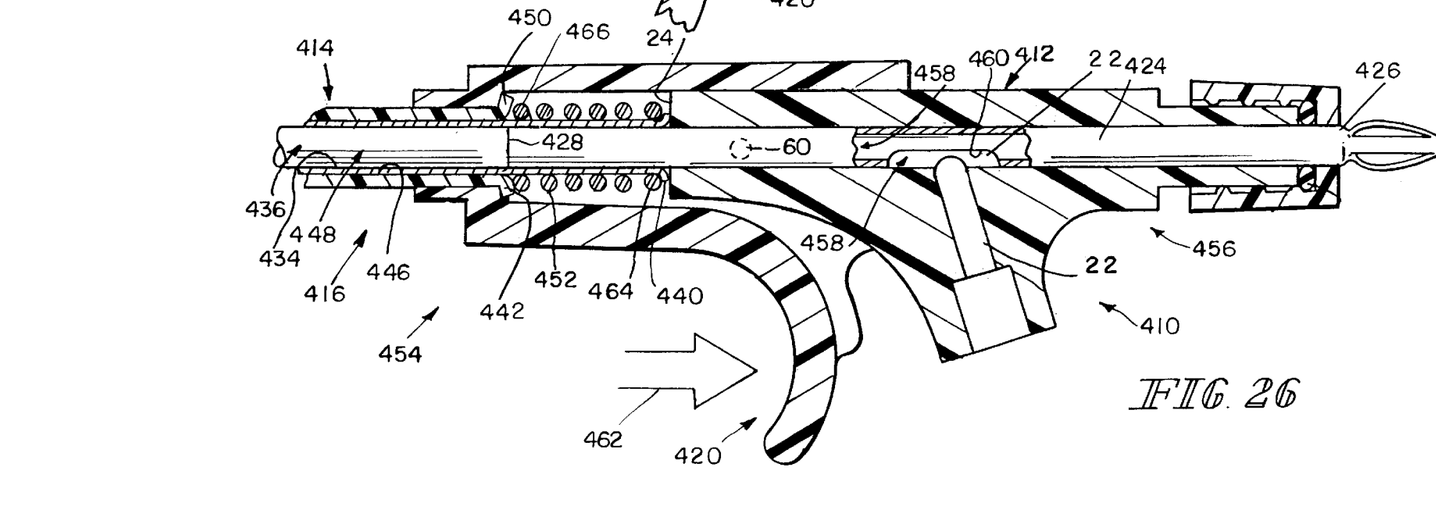
FIG. 26 is a partial sectional view similar to FIG. 25 showing the trigger and outer cannula being retracted relative to the inner cannula.

Outer cannula 416 includes a proximal end 442 positioned adjacent to trigger portion 420 and a distal end 444 spaced apart from trigger portion 420. Outer cannula 416 further includes an inner surface 446 that defines an interior region 448. The inner cannula 414 extends through interior region 448 of outer cannula 416 as shown in FIGS. 24–26. The proximal end 442 of outer cannula 416 includes a flange 450.

The lavage 410 further includes a biasing member or spring 452 that includes a first end 464 engaged with flange 440 of inner cannula 414 and a second end 466 engaged with flange 450 of outer cannula 416 as shown in FIGS. 24–26. The flange 450 of outer cannula 416 engages trigger portion 420 so that spring 452 biases proximal end 430 of inner cannula 414 away from proximal end 442 of outer cannula 416 as shown in FIGS. 25 and 26.

The inner cannula 414, outer cannula 416, trigger portion 420, instrument 422, and spring 452 comprise a first portion 454 of lavage 412. The first portion 454 is a self-contained unit.

The lavage 410 also includes a second portion 456 comprised of conduit piece 412 and valve mechanism 418. The first and second portions 454, 456 are connected by sliding support tube 424 through interior region 436 of inner cannula 414 and snap fitting detent or projection 60 into slot 27 formed in conduit piece 412 as shown in FIG. 25. Support tube 424 is slid into interior region 436 of inner cannula 414 until front end 24 of conduit piece 412 engages flange 440 of inner cannula 414. The support tube 424 is tapered as discussed above to provide a good seal with inner cannula 414. The support tube 424 includes a passageway 458 and an opening 460 that permits fluid, gas, and solid communication between interior region 436 of inner cannula 414 and channels 20, 22 of conduit piece 412 as shown in FIGS. 25 and 26.

The surgeon may select from a variety of first instrument portions 454 to connect to the second handle portion 456 based on the type of instrument 422 required. Thus, a single handle portion 456 can be used with a variety of instrument portions 454. In the illustrated embodiment, the instrument portions 454 are easily snap fit onto handle portion 456. In alternative embodiments, other types of connections may be used between separate handle and instrument portions of a lavage.

The surgeon operates lavage 410 in an identical manner as lavages 10, 110 discussed earlier. To expose instrument 422, the surgeon presses inwardly on trigger portion 420 inwardly in direction 462, as shown in FIG. 26, so that outer cannula 416 is moved in direction 462 relative to inner cannula 414. As discussed above with reference to lavages 10, 110, moving outer cannula 416 in direction 462 relative to inner cannula 414 exposes instrument 422 so that the instrument 422 may be used by the surgeon. The surgeon may also actuate valve mechanism 418 with the same hand that operates trigger portion 420 to provide vacuum and saline functions.

In alternative embodiments of the present invention, a bipolar electrical connector such as connector 166 shown in FIGS. 1b and 2b may be used instead of a monopolar connector on a lavage such as lavage 410.

Although the invention has been described with reference to certain embodiments, it is understood that variations exist within the scope and spirit of the present invention.

What is claimed is:

1. A lavage for suction and removal of body tissues in a patient, the lavage comprising:
    a shield formed to include an opening,
    a cannula defining a cannula interior, the cannula having a proximal end and a distal end, the distal end being insertible and positionable in a patient's body, and the cannula defining a cannula opening to permit access to the cannula interior for capture of body tissue in the cannula interior, the cannula being positioned to lie in the opening formed in the shield,
    an instrument coupled to the cannula,
    a shield actuator adapted to be engaged by a user, the shield actuator being coupled to the shield to move the shield relative to the cannula between a first position wherein the shield covers the instrument and a second position wherein the shield is spaced apart from the instrument,
    a valve connected to the cannula for independent actuation to control irrigation and vacuum within the cannula, regardless of movement or lack of movement of the shield, the cannula and valve being integrated into a rigid structure to be held in a user's hand such that movement of the rigidly coupled cannula and valve by the user's hand allows the distal end of the cannula to be accurately positioned at a specific location in the patient's body, and the valve and shield actuator beings operable by the hand of the user that moves the rigidly coupled valve and cannula to accurately position the distal end of the cannula in the patient's body.

2. The lavage of claim 1, wherein the interments is compressible and the shield includes an inner surface configured to compress the instrument when the shield is in the first position.

3. The lavage of claim 2, wherein the instrument is a loop and the loop is flattened by the shield when the shield is in the first position.

4. The lavage of claim 2, wherein the instrument includes first and second portions, the first and second portions beings positioned adjacent to each other when the shield is in the first position and spaced apart from each other when the shield is in the second position.

5. The lavage of claim 4, wherein the instrument includes a grasper, the grasper includes first and second legs coupled to the cannula and first and second feet coupled to the first and second legs, respectively, the first and second feet are engaged when the shield is in the first position and spaced apart when the shield is in the second position.

6. The lavage of claim 4, wherein the instrument includes scissors, the scissors include first and second blades, the first and second blades are engaged when the shield is in the first position and spaced apart when the shield is in the second position.

7. The lavage of claim 1, wherein the instrument includes a rectangular cross section.

8. The lavage of claim 1, wherein the instrument includes a double convex cross section.

9. The lavage of claim 1, wherein the shield actuator is positioned adjacent to the rigid structure.

10. The lavage of claim 1, wherein the cannula opening is at the distal end of the cannula.

11. The lavage of claim 1, wherein the instrument includes a proximal end coupled to the distal end of the cannula and a distal end spaced apart from the cannula.

12. The lavage of claim 11, wherein the shield includes a proximal end positioned adjacent the rigid body and a distal end spaced apart from the rigid body, the distal end of the shield extends past the distal end of the instrument when the shield is in the first position and the distal end of the instrument extends past the distal end of the shield when the shield is in the second position.

13. The lavage of claim 1, further comprising a biasing member having a first end coupled to the cannula and a second end coupled to the shield to bias the shield relative to the cannula.

14. The lavage of claim 13, wherein the shield is fixed to the shield actuator and the biasing member includes a first end engaged with the rigid body and a second end engaged with the shield actuator to bias the shield and shield actuator relative to the cannula, rigid body, and instrument.

15. The lavage of claim 13, wherein the shield includes a flange, the cannula includes a flange, and the biasing member includes a first end engaged with the flange of the cannula and a second end engaged with the flange of the shield to bias the shield relative to the cannula.

16. The lavage of claim 13, wherein the biasing member is a spring.

17. The lavage of claim 1, wherein shield, shield actuator, instrument, and cannula comprise a first portion of the lavage and the valve comprises a second portion of the lavage and the first portion of the lavage is a self-contained unit that is connected to the second portion of the lavage.

18. The lavage of claim 17, wherein the first portion is snap fit to the second portion.

19. The lavage of claim 1, further comprising an electrical connector linked to the cannula to provide electrocautery current to the instrument.

20. A lavage for suction and removal of body tissues in a patient, the lavage comprising:
    a cannula defining, a cannula interior, the cannula having, a proximal end and a distal end, the distal end being insertible and positionable in a patient's body, and the cannula defining, a cannula opening to permit access to the cannula interior for capture of body tissue in the cannula interior,
    an instrument coupled to the cannula,
    a shield formed to include an opening, the cannula being positioned within the opening of the shield, the shield being movable to move the shield relative to the cannula between a first position wherein the shield covers the instrument and a second position wherein the shield is spaced apart from the instrument, and
    a valve connected to the cannula for independent actuation to control irrigation and vacuum within the cannula, regardless of movement or lack of movement of the shield, the valve and shield being operable by a hand of the user that moves the valve and cannula to accurately position the distal end of the cannula in the patient's body.

21. The lavage of claim 20, wherein the instrument is compressible and the shield includes an inner surface configured to compress the instrument when the shield is in the first position.

22. The lavage of claim 21, wherein the instrument is a loop and the loop is flattened by the shield when the shield is in the first position.

23. The lavage of claim 21, wherein the instrument includes first and second portions, the first and second portions being positioned adjacent to each other when the shield is in the first position and spaced apart from each other when the shield is in the second position.

24. The lavage of claim 23, wherein the instrument includes a grasper, the grasper includes first and second legs coupled to the cannula and first and second feet coupled to the first and second legs, respectively, the first and second feet are engaged when the shield is in the first position and spaced apart when the shield is in the second position.

25. The lavage of claim 23, wherein the instrument includes scissors, the scissors include first and second blades, the first and second blades are engaged when the shield is in the first position and spaced apart when the shield is in the second position.

26. The lavage of claim 20, wherein the instrument includes a rectangular cross section.

27. The lavage of claim 20, wherein the instrument includes a double convex cross section.

28. The lavage of claim 20, further comprising a shield actuator positioned adjacent to the valve.

29. The lavage of claim 20, wherein the cannula opening is at the distal end of the cannula.

30. The lavage of claim 20, wherein the instrument includes a proximal end coupled to the distal end of the cannula and a distal end spaced apart from the cannula.

31. The lavage of claim 30, wherein the shield includes a proximal end spaced apart from the instrument and a distal end, the distal end of the shield extends past the distal end of the instrument when the shield is in the first position and the distal end of the instrument extends past the distal end of the shield when the shield is in the second position.

32. The lavage of claim 20, further comprising a biasing member having a first end coupled to the cannula and a second end coupled to the shield to bias the shield relative to the cannula.

33. The lavage of claim 32, wherein the shield includes a flange, the cannula includes a flange, and the biasing member includes a first end engaged with the flange of the cannula and a second end engaged with the flange of the shield to bias the shield relative to the cannula.

34. The lavage of claim 32, wherein the biasing member is a spring.

35. The lavage of claim 30, wherein shield, instrument, and cannula comprise a first portion of the lavage and the valve comprises a second portion of the lavage and the first portion of the lavage is a self-contained unit that is connected to the second portion of the lavage.

36. The lavage of claim 35, wherein the first portion is snap fit to the second portion.

37. The lavage of claim 30, further comprising an electrical connector linked to the cannula to provide electrocautery current to the instrument.

* * * * *